(12) United States Patent
Hirano et al.

(10) Patent No.: US 7,888,265 B2
(45) Date of Patent: Feb. 15, 2011

(54) METHOD FOR ASSAYING COPPER IN SILICON WAFERS

(75) Inventors: Katsuya Hirano, Tokyo (JP);
Mohammad B. Shabani, Tokyo (JP)

(73) Assignee: Sumco Corporation, Tokyo (JP)

( * ) Notice: Subject to any disclaimer, the term of this patent is extended or adjusted under 35 U.S.C. 154(b) by 1031 days.

(21) Appl. No.: 11/708,770

(22) Filed: Feb. 20, 2007

(65) Prior Publication Data

US 2007/0207616 A1 Sep. 6, 2007

(30) Foreign Application Priority Data

Feb. 22, 2006 (JP) .............................. 2006-045031

(51) Int. Cl.
*H01L 21/302* (2006.01)
*H01L 21/461* (2006.01)

(52) U.S. Cl. ................. 438/692; 438/745; 438/754

(58) Field of Classification Search ................. None
See application file for complete search history.

(56) References Cited

U.S. PATENT DOCUMENTS

| | | | | |
|---|---|---|---|---|
| 4,053,335 A | * | 10/1977 | Hu | .............................. 438/143 |
| 5,233,191 A | * | 8/1993 | Noguchi et al. | ................. 850/1 |
| 5,970,366 A | * | 10/1999 | Okonogi | ..................... 438/471 |
| 6,146,909 A | * | 11/2000 | Antol et al. | ..................... 438/14 |
| 6,174,740 B1 | * | 1/2001 | Ohta et al. | ..................... 438/14 |
| 6,423,556 B1 | * | 7/2002 | Koveshnikov et al. | ......... 438/14 |
| 6,620,632 B2 | * | 9/2003 | Koveshnikov et al. | ......... 438/14 |
| 6,632,688 B2 | * | 10/2003 | Koveshnikov | ................. 438/14 |
| 6,649,427 B2 | * | 11/2003 | Koveshnikov et al. | ......... 438/14 |
| 7,399,635 B2 | * | 7/2008 | Hellin et al. | ..................... 436/5 |
| 7,686,973 B2 | * | 3/2010 | Hirano et al. | ................. 216/84 |
| 2003/0073240 A1 | * | 4/2003 | Mizuno | ......................... 436/4 |
| 2004/0161943 A1 | * | 8/2004 | Ren et al. | ..................... 438/758 |
| 2004/0232111 A1 | * | 11/2004 | Hirano et al. | ................. 216/83 |
| 2005/0045593 A1 | * | 3/2005 | Ren et al. | ..................... 216/83 |
| 2007/0007245 A1 | * | 1/2007 | Uchida et al. | ................. 216/79 |
| 2007/0207616 A1 | * | 9/2007 | Hirano et al. | ............... 438/692 |
| 2007/0207617 A1 | * | 9/2007 | Hey et al. | ..................... 438/692 |
| 2008/0047934 A1 | * | 2/2008 | Hirano et al. | ................. 216/99 |

FOREIGN PATENT DOCUMENTS

| | | |
|---|---|---|
| JP | 09-064133 | 3/1997 |
| JP | 10-223713 | 8/1998 |
| JP | 2004-335955 | 11/2004 |

\* cited by examiner

*Primary Examiner*—Allan Olsen
(74) *Attorney, Agent, or Firm*—Kolisch Hartwell, PC

(57) ABSTRACT

This method for assaying copper in silicon wafers includes the steps of: forming a polysilicon layer on the surface of a p-type silicon wafer having the same characteristics as the silicon wafers being assayed; heat treating the p-type silicon wafer after it has been polished; dissolving the polysilicon layer on the heat-treated p-type silicon wafer with a mixed acid composed of at least hydrofluoric acid and nitric acid; and quantitatively determining the copper components within the mixed acid following dissolution of the polysilicon layer.

5 Claims, 5 Drawing Sheets

METHOD FOR ASSAYING COPPER IN SILICON WAFERS

BACKGROUND OF THE INVENTION

1. Field of the Invention

Copper exerts a large influence on the characteristics of silicon wafers. The present invention relates to a method for assaying copper in silicon wafers which is capable of the quantitative, accurate and highly sensitive detection of copper in silicon wafers. In particular, the present invention relates to a technique suitable for detecting low concentrations of copper below $10^{11}$ atoms/cm$^2$ that are present in high-concentration boron-doped silicon substrates containing at least $3 \times 10^{18}$ atoms/cm$^3$ of boron.

This application claims priority from Japanese Patent Application No. 2006-45031 filed on Feb. 22, 2006, the content of which is incorporated herein by reference.

2. Background Art

In silicon wafers employed as substrates for semiconductor devices and the like, higher circuit integration and device scaling have made it imperative to lower the levels of metallic impurities (e.g., iron, nickel, chromium, copper) in the silicon wafers that seriously degrade device performance. Contamination by metallic impurities in silicon wafer fabrication is thought to arise in the polishing operation on p-type silicon wafers; copper in the polishing slurry diffuses into the bulk material of the wafer, leading to copper contamination. Among the contaminating metals that emerge, copper has a very rapid diffusion rate and easily diffuses into the interior of the silicon substrate. Because such diffused copper degrades the device characteristics (e.g., electrical properties), it is important to reduce the level of copper and control the process.

Recent improvements in contamination control technology, including the cleaning of silicon substrates, has brought the concentration of silicon substrate-contaminating metals down to about $10^{11}$ atoms/cm$^2$.

In carrying out such measures against copper contamination in p-type silicon wafers, it is important for the copper diffused in the bulk material of the silicon wafer to be quantitatively determined to a high precision and accuracy in each step. The techniques used for quantifying the copper diffused in the bulk material of a silicon wafer have hitherto been primarily atomic absorption spectroscopy (AAS) and secondary ion mass spectroscopy (SIMS). AAS in particular is capable of high-sensitivity analysis. AAS is employed using what is known as the total dissolution method in which a portion of a polished silicon wafer is gas-etched with a mixed acid of hydrofluoric acid and nitric acid or a mixed acid of hydrofluoric acid, nitric acid and sulfuric acid, and the decomposition residues after the silicon wafer has dissolved are analyzed.

Such methods have a number of drawbacks. Measurement is very troublesome to carry out, and additional contamination sometimes occurs during pre-treatment prior to measurement. Moreover, because all such methods involve destroying the substrate, re-use of the substrate is impossible.

In this connection, the applicant earlier proposed, as a way of non-destructively analyzing semiconductor substrates, a method for detecting the copper concentration at the interior of a semiconductor substrate (Patent Document 1). This method is exemplified by the LTD (Low temperature diffusion) method which involves heating the silicon substrate to a temperature of 600° C. or less so as to induce copper present within the silicon substrate to diffuse out and collect at the front and rear sides of the substrate, and analyzing the front and rear sides by AAS or total reflection fluorescent X-ray analysis (TXRF). In this method, when the silicon substrate has a p-type conductivity, heating at 500° C. in an open air atmosphere for 15 minutes will result in sufficient diffusion of the copper.

In another method, a polysilicon layer is formed on the polished silicon wafer, the copper in the bulk material is diffused into this polysilicon layer by heat treatment, and the copper within the polysilicon layer to which copper has been diffused is then analyzed (Patent Documents 2 and 3).

Hence, three methods are commonly known for quantitatively determining copper that has diffused into the bulk material in polishing operations: a method in which polysilicon (Poly-Si) is applied to the polished silicon wafer, heat treatment is applied to diffuse copper within the bulk material into the Poly-Si layer, and the copper within the Poly-Si layer is analyzed; an LTD method in which the polished silicon wafer is heat-treated on a hot plate, outwardly diffusing the copper to the surface, and the surface copper is analyzed; and a total dissolution method in which part of the polished silicon wafer is subjected to gas etching with a mixture of hydrofluoric acid and nitric acid or with a mixture of hydrofluoric acid, nitric acid and sulfuric acid, and the decomposition residues after dissolution of the silicon wafer are analyzed.

However, the above prior-art methods for quantifying the copper diffused in the bulk material of a silicon wafer pose a number of challenges with regard to the precision and accuracy of detection. For example, in a method that involves forming a polysilicon layer on the polished silicon wafer and thermally diffusing copper into this polysilicon layer by heat treatment, and then analyzing, polysilicon is applied to the silicon wafer after the polishing operation, leading to the formation of a polysilicon layer on both sides of the silicon wafer. Hence, the copper that has diffused into the bulk material because of polishing disperses out to the polysilicon layers on either side of the wafer during heat treatment, rendering high-precision analysis impossible.

Also, when polysilicon is applied to the polished silicon wafer, the amount of copper that was already diffused in the silicon wafer prior to polishing becomes unclear. Because quantitative determination of the copper is possible only after polishing, the amount of copper that diffused into the silicon wafer during the polishing step cannot be determined.

In the LTD method which involves heat-treating the polished silicon wafer on a hot plate and analyzing the copper that has outwardly diffused to the surface, when the wafer is heat-treated on a hot plate, sometimes 100% of the copper in high boron concentration wafers ($p^+$, $p^{++}$) does not diffuse outward to the wafer surface, thus making it difficult to accurately and rapidly determine the total copper in the wafer. Moreover, in all p-type silicon wafers, when the wafer is heat treated on a hot plate, the copper does not diffuse outward to the front and rear sides of the wafer and disperses, making high-sensitivity analysis impossible.

In a total dissolution method in which a portion of a polished silicon wafer is dissolved with a mixed acid and the dissolution residues are analyzed, to carry out quantitative analysis of the metallic impurities in the residues with an atomic absorption spectrophotometer or an inductively coupled plasma mass spectrometer, it is necessary to remove the large amount of silicon present in the recovered solution. Removing such silicon by sublimation involves dissolving the silicon with a mixed acid such as hydrofluoric acid, nitric acid and sulfuric acid and carrying out concentration. However, because such an approach requires the use of a large amount of chemicals, metallic impurities present in the chemicals are also included during quantitative analysis.

When concentration is carried out over an extended period of time, there is even a possibility that impurities in the atmospheric air will be taken up, making an accurate determination difficult to carry out. Furthermore, because the silicon wafer after it has been polished is completely dissolved, the amount of copper diffused within the silicon wafer before polishing is unclear; it is possible only to determine the amount of copper in the wafer after it has been polished.

It is therefore an object of the present invention to provide a method for assaying the copper within a silicon wafer, which method involves no complicated operations and can accurately detect to a high sensitivity the concentration of copper in a silicon wafer.

Patent Document 1: Japanese Patent Application, First Publication No. H09-64133

Patent Document 2: Japanese Patent Application, First Publication No. H10-223713

Patent Document 3: Japanese Patent Application, First Publication No. 2004-335955

SUMMARY OF THE INVENTION

The method for assaying copper in silicon wafers of the present invention includes: forming polysilicon layers on the surfaces of a p-type silicon wafer having the same characteristics as the silicon wafers being assayed; polishing the p-type silicon wafer and then subjecting the p-type silicon wafer to a heat treatment; and dissolving the polysilicon layer on the heat-treated p-type silicon wafer with a mixed acid including at least hydrofluoric acid and nitric acid, and quantitatively determining the copper components within the mixed acid after dissolution of the polysilicon layer.

In the method for assaying copper in silicon wafers of the present invention, the characteristics of the silicon wafer may be at least the electrical resistivity, the orientation of the crystal axis, and the oxygen concentration.

The heat treatment may be carried out, according to the dopant concentration of the silicon wafer, in a temperature range and over a treatment time which are required for the copper in the silicon wafer to migrate to the polysilicon layer.

Dissolution by the mixed acid may lower the thickness of the polysilicon layer in a thickness range at which the copper in the polysilicon layer is detectable.

Quantitative determination of the copper components may be carried out by atomic absorption spectrometry or inductively coupled plasma mass spectroscopy.

The polysilicon layers may be formed on the front surface and the rear surface of the p-type silicon wafer, and the polysilicon layer on one surface may be removed by the polishing.

Polysilicon layers may be formed on the surfaces of two or more p-type silicon wafers having the same characteristics as the silicon wafers being assayed, and the method may further comprise dissolving the polysilicon layer on at least one p-type silicon wafer which is not subjected to the polishing, with a mixed acid including at least hydrofluoric acid and nitric acid, and quantitatively determining the copper components within the mixed acid after dissolution of the polysilicon layer, thereby, obtaining the amount of copper components before polishing.

In prior-art methods which involves applying polysilicon layers onto a polished silicon wafer, heat-treating and analyzing the copper in the polysilicon layers, because the amount of copper diffused within the silicon wafer before it is polished is unclear, it has been possible only to quantitatively determine the amount of copper after polishing. Typically, at least two silicon wafers with the same characteristics are furnished as assay samples. Polysilicon layers are deposited on each wafer, and at least one of the wafers is polished and the other wafer is left unpolished as a control. Next, the polysilicon layer on each wafer is dissolved in the above-described test liquid, and the amounts of copper in the respective test solutions are detected and compared. In this way, the amount of copper before and after polishing can be quantitatively determined, making it possible to identify only the amount of copper which contaminates the wafer in the polishing step.

Moreover, in the above-described prior-art methods, copper gettering occurs as a result of the boron concentration. The influence of such gettering has made accurate detection in low-resistance wafers impossible. However, unlike such prior-art methods, in the assay method of the present invention, as subsequently described, the amount of copper can be accurately detected without being influenced by the boron concentration. By employing the above-described assay method on $p^-$-, $p^+$- and $p^{++}$-type wafers having differing boron concentrations (dopant concentrations), the state of contamination in the polishing step and accurate copper amounts can be determined regardless of differences in copper amount detection due to wafer type; that is, regardless of the boron concentration.

As used herein, "$p^{++}$ type wafer" refers to a low-resistance wafer having a boron concentration of about $10^{19}$ atoms/cm$^3$ and a resistivity of about 1 to 10 mΩ·cm, "$p^+$ type wafer" refers to a low-resistance wafer having a boron concentration of about $10^{18}$ atoms/cm$^3$ and a resistivity of about 10 to 1,000 mΩ·cm, and "$p^-$ type wafer" refers to a high-resistance wafer having a boron concentration of about $10^{15}$ atoms/cm$^3$ and a resistivity >1 Ω·cm. The boron concentrations are values corresponding to the resistivity.

In prior-art detection techniques, one difficulty has been that applying polysilicon layers to a polished silicon wafer results in the formation of polysilicon layers on both sides of the silicon wafer. Copper that has diffused into the bulk material in the polishing operation thus disperses and diffuses out to the polysilicon layers on both sides of the wafer under heat treatment, making highly sensitive copper analysis impossible. In contrast, in the present invention, when a polysilicon layer is provided on each of the front surface and the rear surface of the reference silicon wafer before polishing, the polysilicon layer on the one side is polished and removed and the polysilicon layer remains on only the other side of the silicon wafer after polishing. Subsequent heat treatment on a hot plate causes all the copper during polishing to diffuse to the polysilicon layer remaining on the other side of the wafer, enabling highly sensitive copper analysis to be carried out.

As for the prior-art LTD method in which a polished silicon wafer is heat-treated on a hot plate and copper in the surface is analyzed, a drawback is that when high-boron-concentration, low-resistance ($p^+$, $p^{++}$) wafers are heat-treated over a hot plate, sometimes 100% of the copper does not diffuse outward to the wafer surface, making quantitative determination impossible. However, by providing polysilicon layers on the reference silicon wafer before polishing, even in high-boron-concentration wafers ($p^+$, $p^{++}$), all of the copper is able to diffuse to the polysilicon layer when the wafer is treat-treated. Hence, by analyzing the copper within this polysilicon layer, accurate quantitative determination of the copper is possible. Heat treatment may be carried out under specific time and temperature conditions, and is not limited to heat treatment over a hot plate.

Up until now, when heat treatment was carried out over a hot plate, the copper diffused and dispersed outward to the front and rear sides throughout all of the p-type wafer, making the copper impossible to analyze at a high sensitivity. However, by providing the polysilicon layers on the front surface and the rear surface of the reference silicon wafer prior to polishing, after the wafer has been polished and the polysilicon layer on the one surface has been removed, the polysilicon layer remains on only one side of the wafer. Because all of the copper that diffused to the polysilicon layer on one side of the wafer during polishing will diffuse outward when heat treatment is subsequently carried out over a hot plate, it becomes possible to analyze the copper at a high sensitivity.

Also, in the prior-art total dissolution method which involves dissolving a portion of a polished silicon wafer and analyzing the dissolved decomposition residues, because the silicon wafer is dissolved in an mixed acid (processing solution) of hydrofluoric acid, nitric acid and sulfuric acid, then concentrated, there is a risk of metallic impurities present in the chemicals being introduced. Moreover, a large amount of processing solution is needed to detect all of the copper, including the copper located deep in the wafer, and this large amount of processing solution takes a long time to concentrate, resulting in a poor efficiency. An additional concern is the possibility of contamination from atmospheric air during concentration of the processing solution. However, because the method of the present invention involves no concentration by chemicals whatsoever, there is no possibility that metallic impurities present in such chemicals or that atmospheric contamination during an extended period of concentration will become incorporated, thus enabling the determination of copper to be efficiently carried out to a higher precision.

The characteristics of the silicon wafer may be at least the electrical resistivity, the orientation of the crystal axis, and the oxygen concentration.

Unless the wafers are ones in which these characteristics are identical, the copper contamination state in the assay method of the present invention will differ from the degree of copper contamination in the actual polishing operation, which is undesirable. Moreover, in the assay method of the present invention, by targeting $p^-$, $p^+$ and $p^{++}$ type wafers in which it has been difficult to accurately determine the state of copper contamination because they have a high concentration of boron, differences in the state of copper contamination due to the dopant concentration are clarified and copper contamination in the polishing operation on these wafers can be accurately determined for the first time.

Heat treatment may be carried out, according to the dopant concentration of the silicon wafer, in a temperature range and over a treatment time required for the copper in the silicon wafer to migrate to the polysilicon layer. Specifically, it is preferable to carry out heat treatment in a temperature range of about 200° C. to about 450° C. and for a treatment time of about 5 minutes to about 60 minutes, or under equivalent temperature and time conditions. For example, in a $p^{++}$ type wafer, copper diffuses to a sufficient degree with heat treatment at 300° C. for 60 minutes, although it is equally possible to carry out heat treatment at 350° C. for 30 minutes, or to carry out low-temperature heat treatment at about 100° C. by extending the treatment time. In a $p^+$ type wafer, sufficient copper diffusion occurs with treatment at 300° C. for 30 minutes or treatment at 350° C. for 20 minutes. In a $p^-$ type wafer, sufficient copper diffusion occurs with treatment at 250° C. for 10 minutes or treatment at 300° C. for 5 minutes. By setting a high temperature, quantitative determination of the copper can be satisfactorily carried out even in a short period of about 1 to 5 minutes.

Here, the treatment time is preferably 60 minutes or less for reasons having to do with the efficiency of the operation, but is preferably 5 minutes or more for sufficiently accurate copper detection. The upper limit in the treatment temperature is preferably 450° C. or less in order to avoid, apart from copper diffusion, large thermal impacts on the wafer which may give rise to undesirable effects, but is preferably 200° C. or more to ensure fully accurate copper detection.

Dissolution by the above-described mixed acid is used to lower the thickness of the polysilicon layer within a thickness range at which the copper in the polysilicon layer is detectable. Specifically, the thickness of the polysilicon layer to be dissolved is preferably 0.1 μm or more, which is a level at which the dissolved copper in the polysilicon layer can be detected to a sufficient accuracy by the subsequently described atomic absorption spectroscopy or inductively coupled plasma mass spectroscopy, although it is more preferable to set the dissolution range to about 1 to 2 μm so as to improve the limit of detection. The upper limit in the thickness range of the polysilicon layer to be dissolved is preferably 2 μm or less, for preventing copper from getting mixed in at the time of detection and because of the amount of solution required for treatment.

Quantitative determination of the copper components may be carried out by atomic absorption spectrometry or inductively coupled plasma mass spectroscopy.

In the method for assaying copper in silicon wafers of the present invention, by heating one of a pair of p-type silicon wafers having the same characteristics as the silicon wafers being assayed and thereby diffusing copper to the polysilicon layer, and by not heating the other p-type silicon wafer so as not to cause copper to diffuse to the polysilicon layer, then quantitatively determining the copper in the polysilicon layer on each silicon wafer, the amount of copper that is diffused within the silicon wafer prior to the polishing operation can be known. Moreover, by comparing the amount of copper in a reference silicon wafer prior to the polishing step with the amount of copper in a reference silicon wafer after the polishing step, the degree to which the silicon wafer has been contaminated with copper in the polishing step can be accurately determined.

PREFERRED EMBODIMENTS

Figure 1:
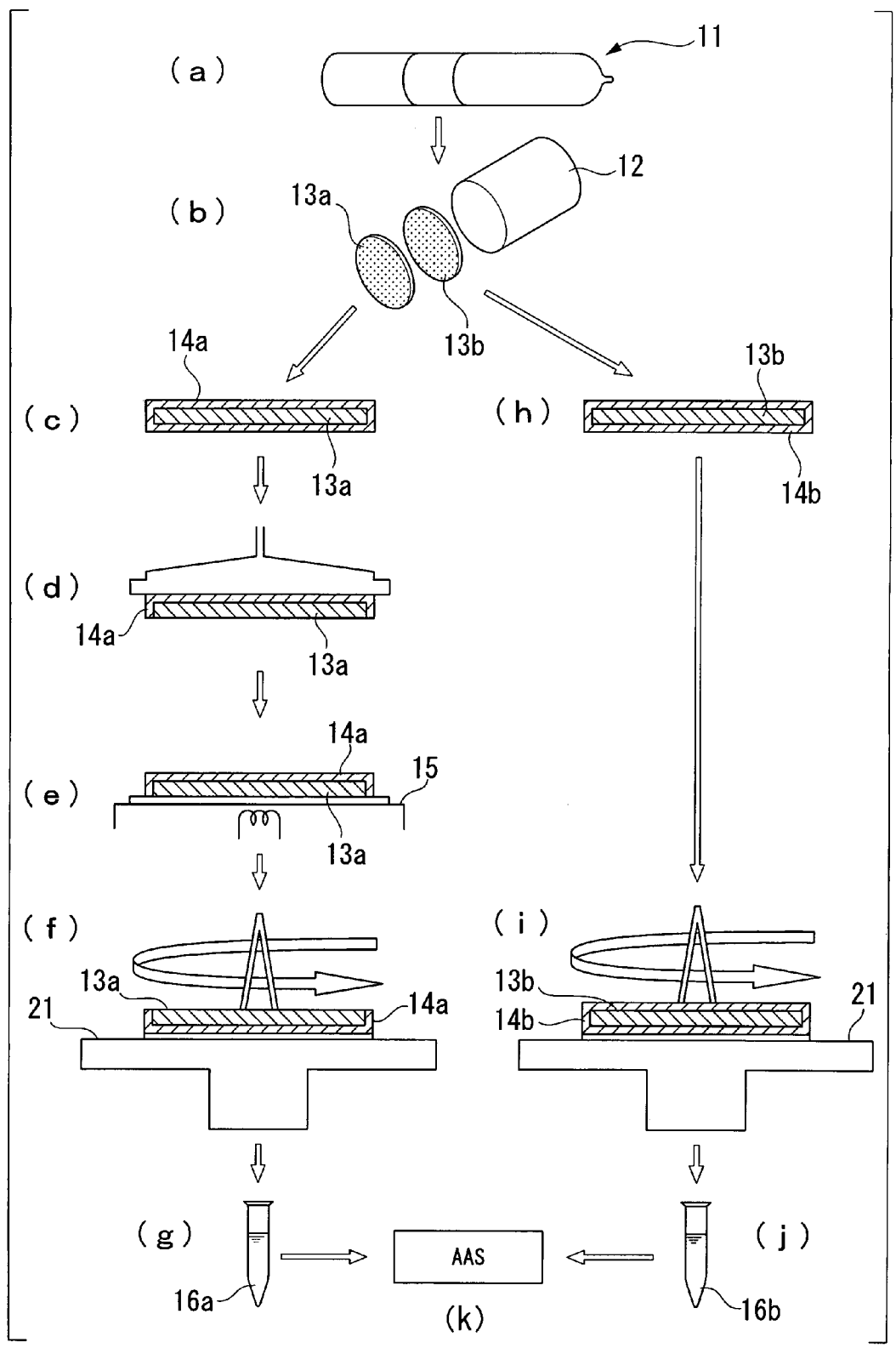
FIG. 1 is a diagram illustrating the method for assaying copper in silicon wafers of the present invention.

As for a first embodiment of the present invention, the sequence of steps for quantitatively determining copper in a silicon wafer by the inventive assay method is described below while referring to an accompanying diagram. FIG. 1 is a diagram illustrating the method for assaying copper in silicon wafers of the present invention. First, a single crystal silicon ingot 11 that has been pulled by the Czochralski (CZ) method, for example, is cut at given positions in accordance with characteristics such as the thermal history during crystal growth, then the outer periphery of the cut ingot is ground a constant thickness, and notches or the like to indicate the orientation of the crystal axis are placed on the ingot, thereby a cylindrical block 12 is formed (FIG. 1(a)).

A plurality of silicon wafers of a predetermined thickness are sliced from this single crystal silicon block 12 and, after subsequently passing through steps such as edge grinding, lapping and etching, they are rendered into the state just prior to the polishing operation. Two silicon wafers 13a and 13b for assaying were selected from this one lot of silicon wafers sharing the same characteristics (electrical resistivity, orientation of crystal axis, and oxygen concentration) (FIG. 1(b)). Polysilicon layers 14a and 14b are formed on the two silicon wafers 13a and 13b for assaying (FIGS. 1(c), 1(h)).

Regarding the formation of the polysilicon layers 14a or 14b, when an oxide film or the like has formed on the surface of the silicon wafer 13a or 13b, the oxide film is removed by cleaning with an aqueous solution of hydrofluoric acid or the like, and then polysilicon layers 14a or 14b having a thickness of about 2 μm, for example, are deposited on the surface of the silicon wafer 13a or 13b.

Next, of the two silicon wafers 13a, 13b for assaying, one side of one silicon wafer 13a is polished under the same conditions as in the polishing step being assayed, thereby removing the polysilicon layer 14a on one side only and exposing the surface of the single crystal silicon wafer 13a on one side only (FIG. 1(d)).

The silicon wafer 13a from which the polysilicon layer 14a has been removed on one side only is then placed with the polysilicon layer 14a facing up and heated to a predetermined temperature using a hot plate 15 or the like (FIG. 1(e)). This heating step of the silicon wafer 13a is achieved by, for example, using a hot plate 15 to heat the silicon wafer 13a for a period from 5 to 60 minutes in a temperature range from 200 to 450° C. The heat treatment conditions (heating temperature and time) here are the conditions at which the copper to be assayed fully diffuses to the polysilicon layer 14a as subsequently described.

Figure 2:
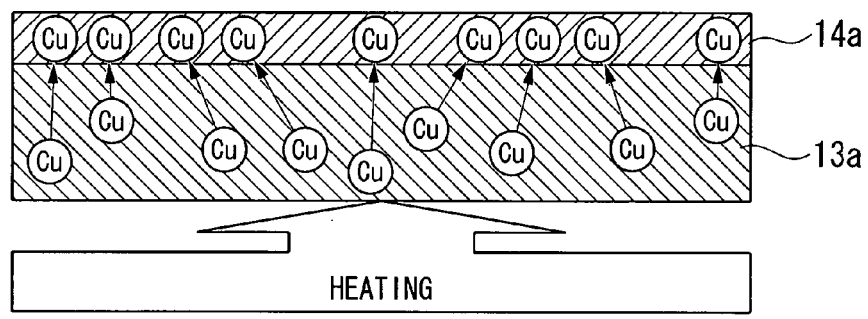
FIG. 2 is a schematic diagram showing copper diffusion in the heat treatment step.

When the silicon wafer 13a is heated in this heating step within a given temperature range for a given length of time, as shown in FIG. 2, the copper which is present as an impurity in the silicon wafer (bulk layer) 13a diffuses at a constant diffusion rate to the polysilicon layer 14a that is formed on the surface of the silicon wafer 13a. In this way, the copper that is present in the silicon wafer 13a prior to the heating step diffuses to and accumulates within the polysilicon layer 14a.

Such diffusion of the copper present in the silicon wafer 13a to the polysilicon layer 14a by heating is particularly effective in $p^-$, $p^+$ and $p^{++}$ type silicon wafers which contain high levels of boron. Of these, $p^-$ type silicon wafers are defined as containing about $10^{15}$ atoms/cm$^3$ of boron and having a resistivity of 1 Ω·cm or more; $p^+$ type silicon wafers are defined as containing about $10^{18}$ atoms/cm$^3$ of boron and having a resistivity of about 10 to 1,000 mΩ·cm; and $p^{++}$ type silicon wafers are defined as containing about $10^{19}$ atoms/cm$^3$ of boron and having a resistivity of about 1 to 10 mΩ·cm.

At the substrate interior of p-type silicon wafers containing a large amount of boron, such as $p^-$-, $p^+$- and $p^{++}$-type silicon wafers, the boron has a negative potential, the copper has a positive potential, and electro statics effect due to the boron and copper make it difficult for the copper to diffuse. Therefore, in silicon wafers containing a high concentration of boron, such as $p^-$-, $p^+$- and $p^{++}$-type wafers, sufficient diffusion of copper to the polysilicon layer cannot be achieved by prior-art heating steps. However, by heating the silicon wafer 13a in a temperature range of from 200 to 450° C. for a period of from 5 to 60 minutes, or under equivalent conditions, according to the present invention, sufficient copper diffusion to the polysilicon layer is achieved.

For example, in a $p^-$-type silicon wafer, heating at 200° C. for about 10 minutes will suffice. In a $p^{++}$-type silicon wafer having an even higher level of copper, sufficient diffusion of the copper to the polysilicon layer is obtained by heating at 450° C. for about 60 minutes. Moreover, in such a heating step, it is preferable to first set a clean silicon wafer containing no impurities on the hot plate 15, place the silicon wafer 13a to be assayed on top of the clean silicon wafer, and carry out heating. In this way, copper contamination in steps other than the polishing step being assayed can be prevented.

Because the polysilicon layer 14a on one side of the wafer is removed by polishing in the polishing step which directly precedes the step in which copper present in the silicon wafer 13a is diffused to the polysilicon layer 14a by heating, the copper that diffuses by heating can be trapped in the polysilicon layer 14a remaining on only one side of the wafer. In this way, the amount of copper which diffuses into the polysilicon layer 14a can be increased, enabling copper analysis that is more precise and sensitive than in the prior art.

Figure 8:
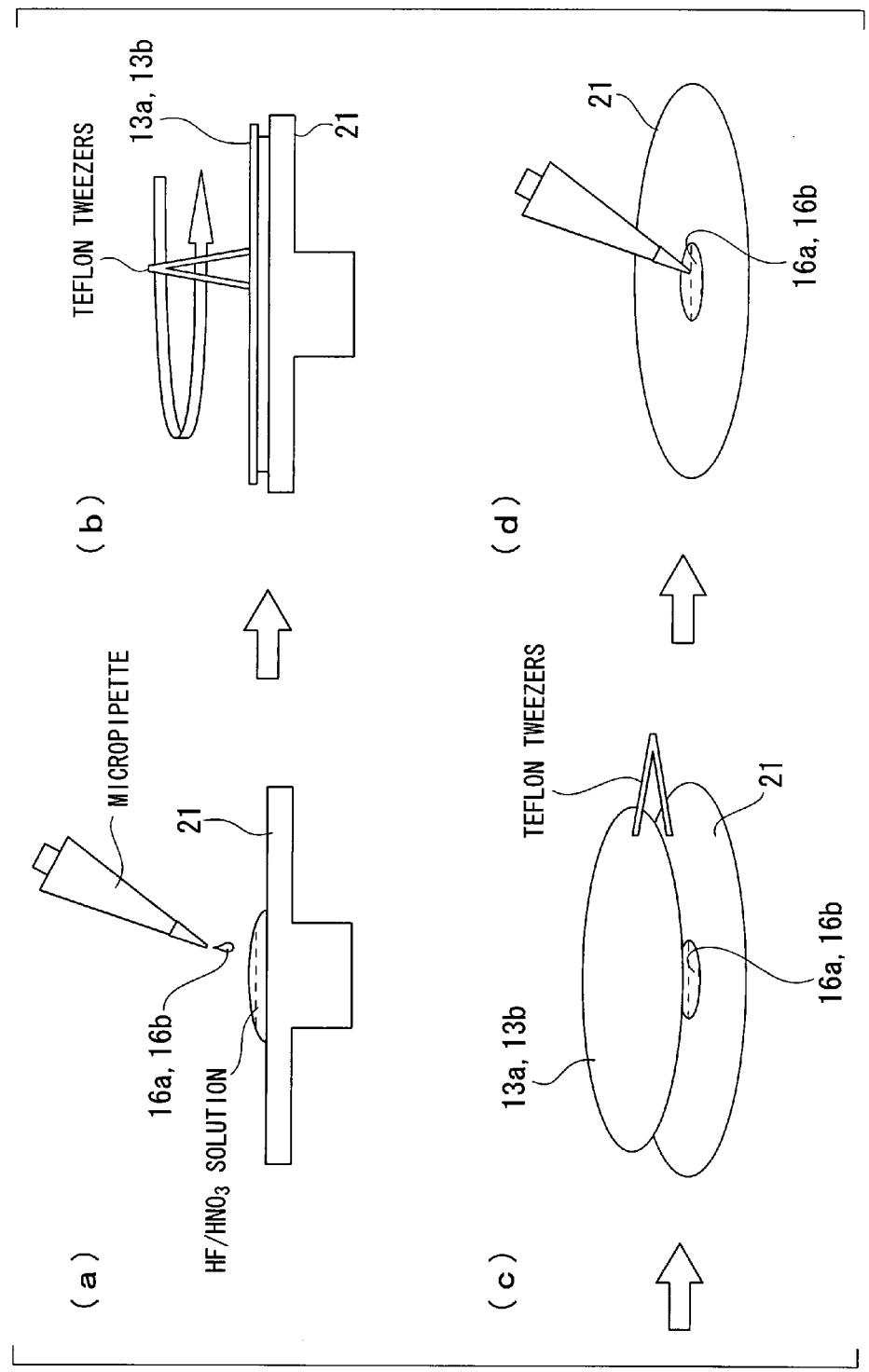
FIG. 8 is a diagram showing an example of the treatment sequence in the dissolution step of the method for assaying copper of the present invention.

After the copper present in the silicon wafer 13a being assayed has been diffused to the polysilicon layer 14a by means of the heating step as described above, a portion (14a) of this silicon wafer 13a is dissolved by etching, and a solution for analysis is recovered (FIG. 1(f)). For the sake of comparison, the other silicon wafer 13b being assayed, which remains in the state immediately after formation thereon of the polysilicon layer 14b, is likewise dissolved in part (14b), and an assay solution is recovered (FIG. 1(i)). FIG. 8 shows an example of the technique (DSE method) in which such a portion is dissolved by etching, and an assay solution is recovered.

According to FIG. 8, first a mixed acid 16a or 16b is added dropwise onto a Teflon (registered trademark) plate 21 (FIG. 8(a)). The silicon wafer 13a or 13b being assayed is then placed on the plate 21 so as to push it against the mixed acid 16a or 16b (bringing the polysilicon layer 14a or 14b into contact with the mixed acid 16a or 16b). Next, the silicon wafer 13a or 13b is rotated so as to dissolve a portion (14a or 14b) of the silicon wafer 13a or 13b in the mixed acid 16a or 16b (FIG. 8(b)). The silicon wafer 13a or 13b is then removed from the plate 21 with tweezers or the like (FIG. 8(c)). The mixed acid (solution or recovered solution) 16a or 16b left on the plate 21 is then recovered (FIG. 8(d)).

The reason why the silicon wafer 13b is not heated in the manner of the silicon wafer 13a prior to such dissolution of the silicon wafer 13a or 13b by a DSE method is that, because heating is required when depositing the polysilicon layer 14b, the copper is sufficiently diffused in the polysilicon layer 14b in much the same way as in the above-described heat treatment. The mixed acid 16a or 16b used in this dissolution step is preferably an mixed acid containing a hydrofluoric acid solution and nitric acid.

In the dissolution step, about 2 μm of the polysilicon layer 14a that has formed on the silicon wafer 13a and about 2 μm of the polysilicon layer 14b that has formed on the silicon wafer 13b are dissolved from the surfaces using the above-described mixed acid or the like (FIGS. 1(f), 1(i)). The polysilicon layer 14a in which the copper present in the silicon wafer 13a has been diffused is thus dissolved by the mixed acid 16a, and the polysilicon layer 14b in which the copper present in the silicon wafer 13b has been diffused is dissolved by the mixed acid 16b.

The copper concentration present in the mixed acid 16a or 16b within which the polysilicon layer 14a or 14b is respectively dissolved in the dissolution step is quantitatively determined by atomic absorption spectroscopy (AAS) or inductively coupled plasma mass spectroscopy (ICP-MS) (FIG. 1(k)).

In using steps such as those described above to heat one of a pair of p-type silicon wafers having the same characteristics as the silicon wafers being assayed so as to diffuse the copper into the polysilicon layer then quantitatively determine the copper in the polysilicon layer of that wafer, one can know the amount of copper that has diffused into the silicon wafer before the polishing step. Moreover, by comparing the amount of copper in the silicon wafer 13b before this polishing step with the amount of copper in the silicon wafer 13a after the polishing step, it is possible to accurately determine the extent to which the silicon wafer is contaminated with copper in the polishing step.

EXAMPLE

The applicant has verified the utility of the present invention. Two silicon wafers of each of three types were furnished for such verification.

Wafer type 1: $p^-$-type silicon wafer having a resistivity of 10 $\Omega \cdot cm$ Wafer type 2: $p^+$-type silicon wafer having a resistivity of 15 $m\Omega \cdot cm$ Wafer type 3: $p^{++}$-type silicon wafer having a resistivity of 8 $m\Omega \cdot cm$ Polysilicon layers were formed to a thickness of 1.5 μm on the front surface and the rear surface of two silicon wafers of each of these wafer types 1 to 3. One of the two silicon wafers of each wafer type 1 to 3 on which a polysilicon layer had been formed was polished, thereby removing the polysilicon layer on one side surface of the wafer. The wafers were then heat-treated at a temperature of 250, 300 or 350° C. for a period of 5, 15, 30 or 60 minutes, thereby heating and diffusing the copper present in the silicon wafer to the polysilicon layer.

Next, silicon wafers 1 to 3 that had passed through these polishing to heating steps were subjected to etching in which 2 μm of the polysilicon layer was removed from the surface of each wafer by a mixed acid composed of hydrofluoric acid and nitric acid, and recovered. The copper in the recovered solution was quantitatively determined using an atomic absorption spectrophotometer (AAS).

Similarly, silicon wafers 1 to 3 that had not undergone such polishing to heating steps were subjected to etching in which 2 μm of the polysilicon layer was removed from the surface of each wafer by a mixed acid composed of hydrofluoric acid and nitric acid, and recovered. The copper in the recovered solution was quantitatively determined using an atomic absorption spectrophotometer (AAS).

Two silicon wafers of each of the above three types having the same characteristics were newly furnished, and polysilicon layers were formed under the same conditions. One of the two silicon wafers of each wafer type 1 to 3 was subjected to polishing to heating steps under the same conditions. Each of silicon wafers 1 to 3 that had passed through these polishing to heating steps and silicon wafers 1 to 3 that had not undergone such polishing to heating steps was completely dissolved in a mixed acid composed of hydrofluoric acid and nitric acid, and the copper in the recovered solution was quantitatively determined using an atomic absorption spectrophotometer (AAS).

Figure 3:
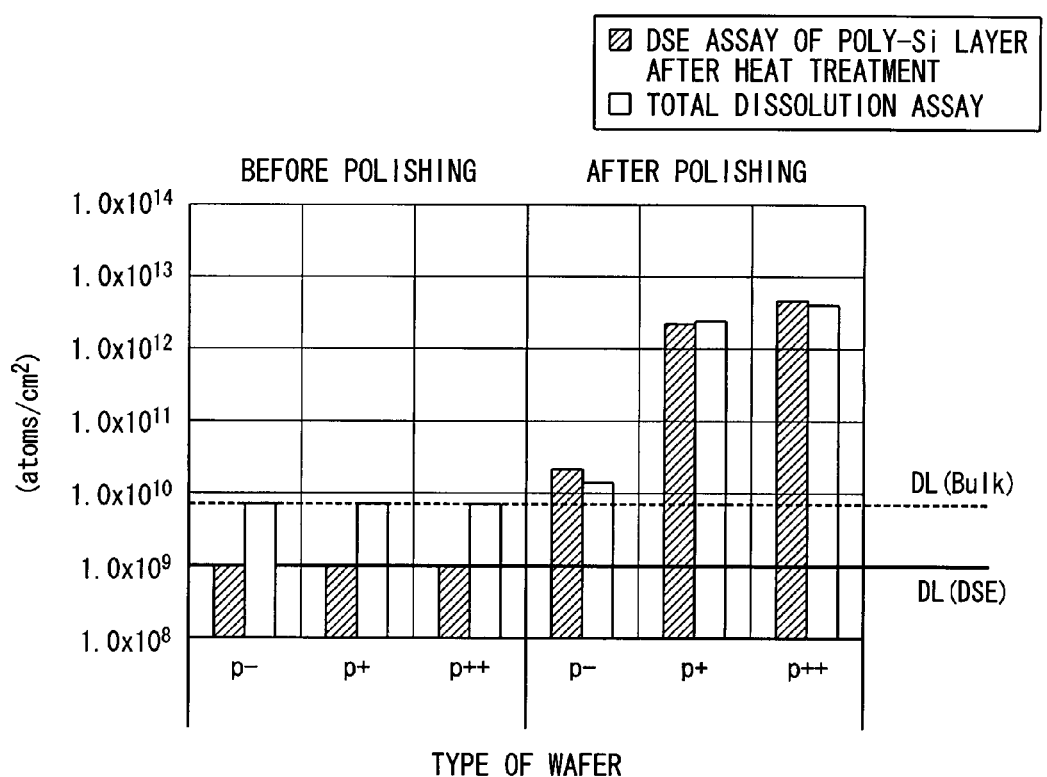
FIG. 3 is a graph showing the results of copper assays before and after polishing.

FIG. 3 shows the results of copper assays, both before and after polishing, in which the level of copper was quantitatively determined after passing through the above steps. It is clear from FIG. 3 that assays of the copper in the polysilicon layer did not detect copper in any of the silicon wafers prior to polishing. However, after polishing, copper at a level of $10^{10}$ atoms/cm$^2$ was found to have diffused to the polysilicon layer in the $p^-$ silicon wafers and copper at a level of $10^{12}$ atoms/cm$^2$ was found to have diffused to the polysilicon layer in the $p^+$ silicon wafers and the $p^{++}$ silicon wafers. Moreover, because a comparison of total dissolution assays with polysilicon layer assays showed that the results from total dissolution assays of the $p^-$ silicon wafers, $p^+$ silicon wafers and $p^{++}$ silicon wafers were at the same level as results from polysilicon layer assays, it is apparent that substantially all of the copper diffuses from the bulk material to the polysilicon layer with heat treatment on a 300° C. hot plate for 60 minutes.

Figure 4:
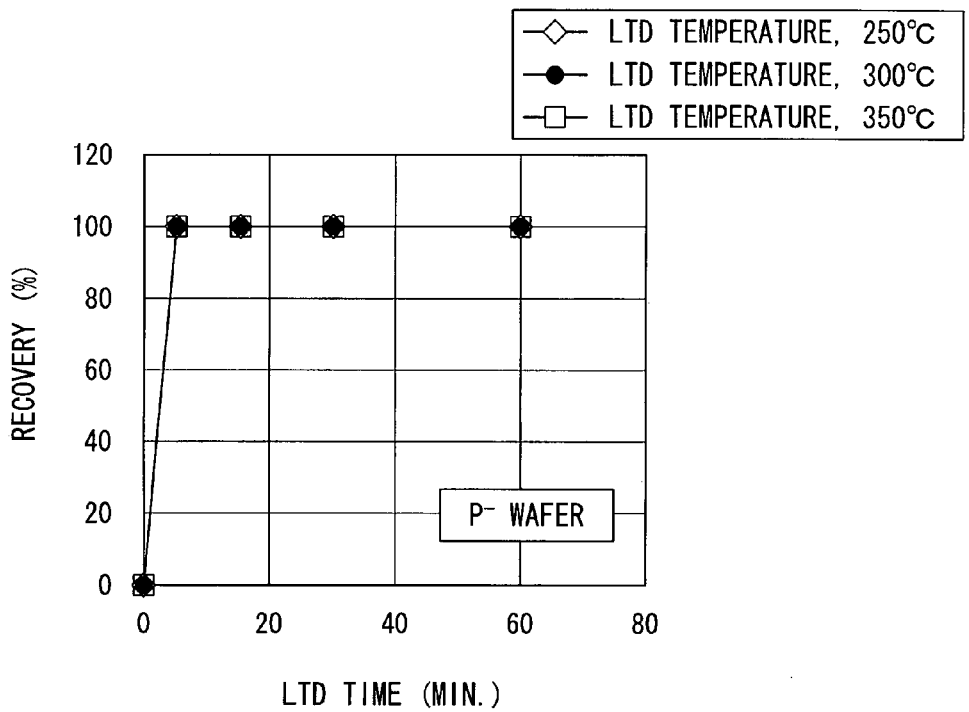
FIG. 4 is a graph showing the relationship between the results of copper assays in the polysilicon layer of a $P^-$ silicon wafer (percent recovery) and the heating time.

FIG. 4 shows the percent recovery results when copper assays of the polysilicon layer were carried out after $p^-$ silicon wafers were heat treated on a hot plate at 250, 300 or 350° C. for 5, 15, 30 or 60 minutes. These results show that, in $p^-$ silicon wafers, substantially 100% of the copper diffuses into the polysilicon layer with heat treatment on a hot plate for at least 5 minutes.

Figure 5:
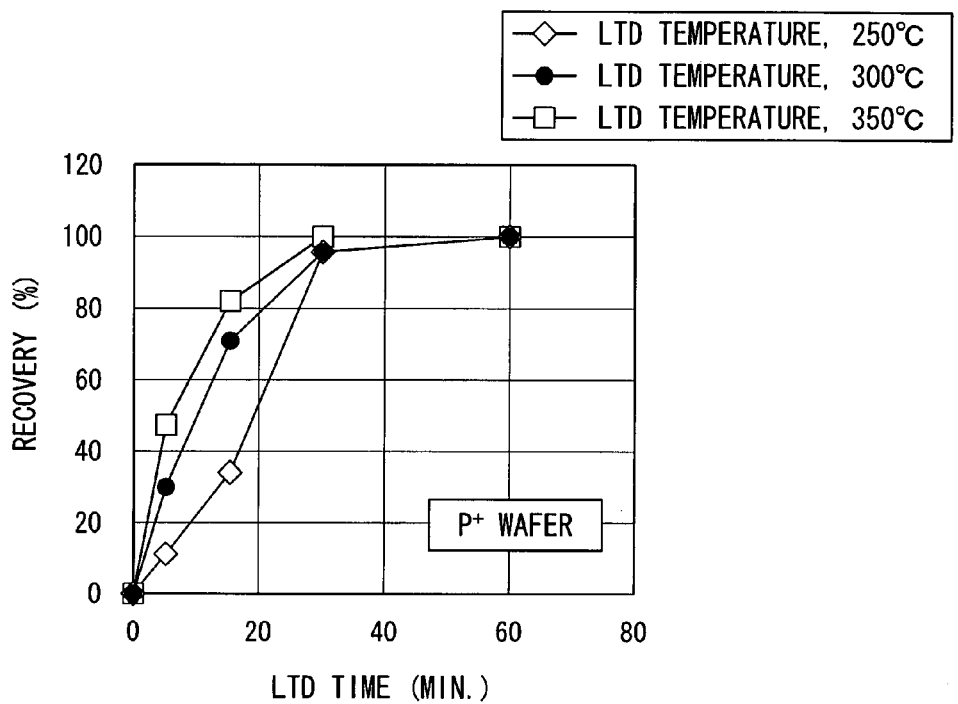
FIG. 5 is a graph showing the relationship between the results of copper assays in the polysilicon layer of a $P^+$ silicon wafer (percent recovery) and the heating time.

FIG. 5 shows the percent recovery results when copper assays of the polysilicon layer were carried out after $p^+$ silicon wafers were heat treated on a hot plate at 250, 300 or 350° C. for 5, 15, 30 or 60 minutes. These results show that, in $p^+$ silicon wafers, at least about 95% of the copper diffuses into the polysilicon layer with heat treatment on a hot plate for at least 30 minutes.

Figure 6:
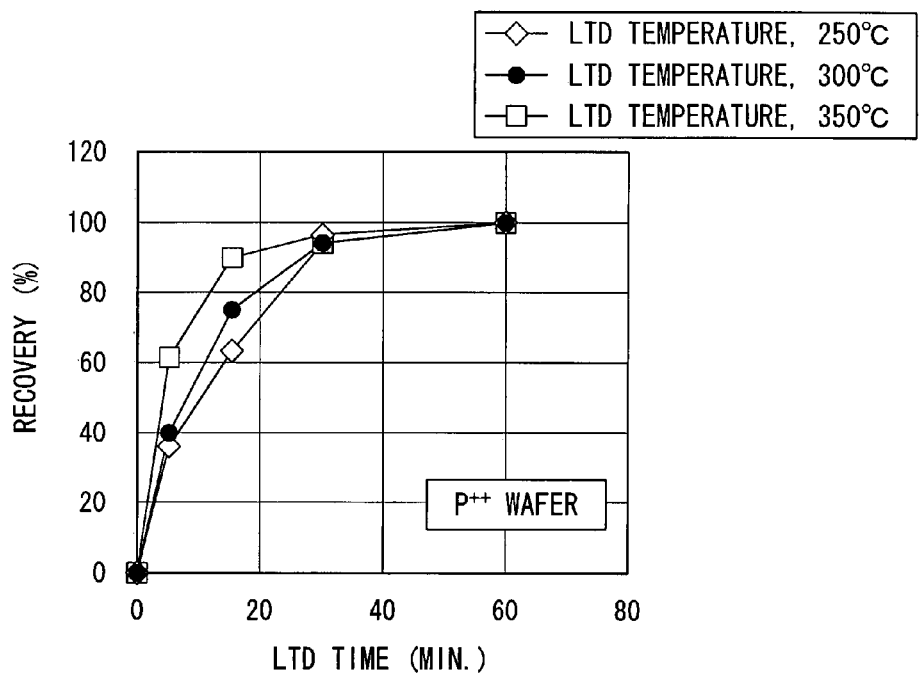
FIG. 6 is a graph showing the relationship between the results of copper assays in the polysilicon layer of a $P^{++}$ silicon wafer (percent recovery) and the heating time.

FIG. 6 shows the percent recovery results when copper assays of the polysilicon layer were carried out after $p^{++}$ silicon wafers were heat treated on a hot plate at 250, 300 or 350° C. for 5, 15, 30 or 60 minutes. These results show that, in $p^{++}$ silicon wafers, at least about 95% of the copper diffuses into the polysilicon layer with heat treatment on a hot plate for at least 30 minutes.

The foregoing results demonstrate that, in p-type silicon wafers, 100% of the copper that diffuses into the bulk material during polishing can be assayed by the formation of a polysilicon layer, polishing and heat treatment. It was thus possible to assay the copper that diffuses to the p-type silicon wafer during polishing at a high sensitivity, a high precision and by relatively simple steps.

Figure 7:
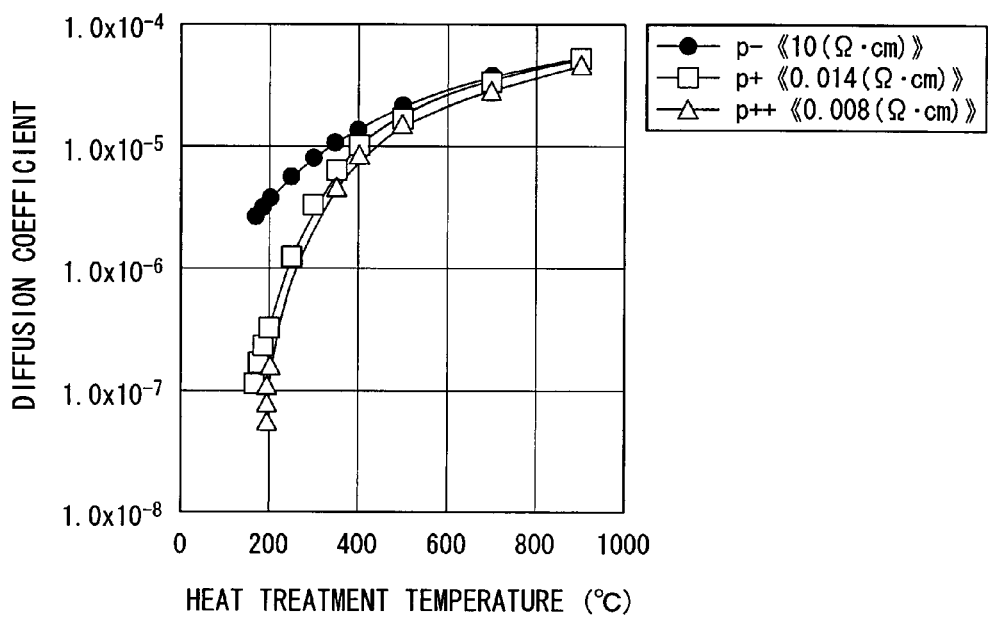
FIG. 7 is a graph of the relationship between the copper diffusion coefficient and the heating temperature.

FIG. 7 shows in a single graph, the results obtained by calculating the relationship between the heat treatment temperatures and copper diffusion coefficients in p-type silicon wafers. The following P-type silicon wafers were used in the calculations:

1. $p^-$ silicon wafers: resistivity, 10 $\Omega \cdot cm$; boron concentration, $3 \times 10^{15}$ atoms/cm$^3$ 2. $p^+$ silicon wafers: resistivity, 0.014 $\Omega \cdot cm$; boron concentration, $5.0 \times 10^{18}$ atoms/cm$^3$ 3. $p^{++}$ silicon wafers: resistivity, 0.008 $\Omega \cdot cm$; boron concentration, $1.0 \times 10^{19}$ atoms/cm$^3$ FIG. 7 shows that in $p^+$ silicon wafers and $p^{++}$ silicon wafers, at a heat treatment temperature of about 200° C., the copper diffusion coefficient is low and there is a possibility that sufficient copper diffusion cannot be obtained. However, when heat treatment is carried out at 400° C. or more, substantially similar diffusion coefficients are obtainable in p⁻ silicon wafers, p⁺ silicon wafers and p⁺⁺ silicon wafers, indicating that sufficient copper diffusion can be carried out.

A preferred embodiment of the present invention has been explained above, but the present invention is not limited to the embodiment. The present invention can be modified by addition, omission, or replacement of the structure to an extent not departing from the scope of the present invention. The present invention is not limited by the above-described explanation, but is limited only by the scope of the appended claims.

What is claimed is:

1. A method for assaying copper in silicon wafers, the method comprising:
   forming polysilicon layers on front surfaces and rear surfaces of two or more p-type silicon wafers having same characteristics as silicon wafers being assayed;
   polishing at least one of the p-type silicon wafers and thereby removing the polysilicon layer on one of the front surface and the rear surface;
   subjecting the polished p-type silicon wafer to a heat treatment at a temperature within a range of 200 to 450° C. for 5 to 60 minutes;
   dissolving the polysilicon layer on the heat-treated p-type silicon wafer with a mixed acid including at least hydrofluoric acid and nitric acid;
   quantitatively determining an amount of copper components within the mixed acid after dissolution of the polysilicon layer on the heat-treated p-type silicon wafer, and thereby obtaining an amount of the copper components after the polishing;
   dissolving the polysilicon layer on at least one of the other p-type silicon wafers which are not subjected to the polishing, with a mixed acid including at least hydrofluoric acid and nitric acid; and
   quantitatively determining an amount of copper components within the mixed acid after dissolution of the polysilicon layer, and thereby obtaining an amount of the copper components before the polishing.

2. The method for assaying copper in silicon wafers according to claim 1, wherein the characteristics of the silicon wafer are at least the electrical resistivity, the orientation of the crystal axis, and the oxygen concentration.

3. The method for assaying copper in silicon wafers according to claim 1, wherein the heat treatment is carried out, according to the dopant concentration of the silicon wafer, in a temperature range and over a treatment time which are required for the copper in the silicon wafer to migrate to the polysilicon layer.

4. The method for assaying copper in silicon wafers according to claim 1, wherein dissolution by the mixed acid lowers the thickness of the polysilicon layer in a thickness range at which the copper in the polysilicon layer is detectable.

5. The method for assaying copper in silicon wafers according to claim 1, wherein quantitative determination of the copper components is carried out by atomic absorption spectrometry or inductively coupled plasma mass spectroscopy.

* * * * *